(12) United States Patent
Draenert (10) Patent No.: US 6,221,477 B1
(45) Date of Patent: Apr. 24, 2001

(54) MATERIAL AND PROCESS FOR PRODUCING THE SAME

(76) Inventor: Klaus Draenert, Gabriel-Max-Strasse 3, DO81545, München (DE)

(*) Notice: Subject to any disclaimer, the term of this patent is extended or adjusted under 35 U.S.C. 154(b) by 0 days.

(21) Appl. No.: 09/259,531

(22) Filed: Mar. 1, 1999

Related U.S. Application Data (62) Division of application No. 08/687,362, filed on Nov. 4, 1996, now Pat. No. 5,958,314.

(30) Foreign Application Priority Data

Feb. 4, 1994 (DE) .................................................. 44 03 509
Feb. 6, 1995 (WO) ...................................... PCTEP9500421

(51) Int. Cl.[7] .................................................. B32B 3/06
(52) U.S. Cl. .......................... 428/307.3; 264/42; 264/49; 264/227; 264/321
(58) Field of Search .............................. 264/42, 49, 227, 264/321, 271.1; 428/307.3

(56) References Cited

U.S. PATENT DOCUMENTS

| 3,700,380 | 10/1972 | Kitrilakis | 264/49 |
| 4,212,839 | 7/1980 | Funahashi | 264/49 |
| 4,226,911 | 10/1980 | Haren | 264/49 |
| 5,522,894 | 6/1996 | Draenert | 623/16 |

FOREIGN PATENT DOCUMENTS

| 2 242 867 | 5/1974 | (DE) . |
| 4 033 291 | 4/1992 | (DE) . |
| 1 139 317 | 1/1969 | (GB) . |
| 1165732 | 6/1989 | (JP) . |

Primary Examiner—Helen L. Pezzuto
(74) Attorney, Agent, or Firm—Westerman, Champlin & Kelly, P.A.

(57) ABSTRACT

A material is disclosed which produced by a process in which a mold is filled of deformable shaped bodies, after which the mold is filled with a base material. The bodies are removed and the solidified base material forms a material of shell-like structures and an interconnecting pore system between the skeleton structures. The material produced by the process can be used as bone replacement materials, implants, filters and drug delivery systems.

5 Claims, 7 Drawing Sheets

MATERIAL AND PROCESS FOR PRODUCING THE SAME

CROSS REFERENCE TO RELATED APPLICATION

This application is a divisional application of application Ser. No. 08/687,362, filed Nov. 4, 1996, now U.S. Pat. No. 5,958,314, which application was based upon a PCT Application No. PCT/EP95/00421, filed Feb. 6, 1995, and which claims priority on Application DE 4403509, filed Feb. 4, 1994.

The invention relates to a process for the preparation of a material comprising a framework consisting of shell-like structures and an interconnecting pore system, a process for the preparation of a material consisting of shaped bodies connected via webs, a process for the preparation of a material which comprises a framework of shell-like structures and whose interconnecting pore system is filled with shaped bodies connected via webs, material producible by means of these processes as well as their use as bone replacement material, artificial bone, implant, filter and drug delivery system.

Lost bone, for instance due to a trauma caused by an accident or after the resection of tumors, after infections or by idiopathically developing bone cysts, has been representing a serious problem for surgeons for a long time. It has, for example, been tried to replace bone artificially, to use animal bone, to process animal bone accordingly such that it is not rejected in humans after it has been inserted or also to preserve bone from humans in freezers and to insert it as frozen homologous bone.

There are various methods for processing animal bone for the use in humans. Ivory, for example, has been also used. A bone replacement which is particularly accepted in surgery is the so-called "Kiel bone chip".

All chemically processed heterologous transplants from animals, however, are incorporated into the host bone incompletely or not at all. The bank bone very often leads to lethal infections, i.a. AIDS infections. Fresh homologous bone transplants are affected by such complications to a much greater extent. In this case, it is even possible to transplant tumors. Therefore, it has repeatedly been tried to develop bone replacement materials and methods by means of which the disadvantages of the immune reaction and the transmission of diseases can be avoided.

In DE-A-39 03 695, a process for the preparation of absorbable ceramics on the basis of tricalcium phosphate is described which can be used as a bone replacement material and in which natural bone material from which the soft tissue has been removed is used as a starting material. Residual organic substance is removed from the bone material by pyrolysis and the remaining bone material consisting of hydroxylapatite is subsequently treated with phosphate carriers and then subjected to sintering. This ignited bovine bone material also exhibits good incorporation properties.

The mentioned materials derived from animals, however, cannot fulfil the demands on bone replacement material with respect to reproducibility of the structure, in particular in view of the material strength and the standardizability of the manufacturing process, and additionally their production is very expensive. Therefore, in medicine it is desirable to produce the used materials, for instance bone replacement materials, fully synthetically. These materials should guarantee maximum strength at a minimum of material and should provide a variety of properties for a variety of indications. It is, for example, desirable to provide a process by means of which on the one-hand bone-like trabecular structures, i.e. a "positive" of the bone, and on the other hand a "negative" of the bone, i.e. shaping negative molds of the medullary cavities of the bone can be produced. By means of such a process, on the one hand the physiological structure of bone could be reproduced and, by means of the negative, on the other hand supporting and guiding frameworks could be provided around which bone grows and which are very rapidly able to take up high loads.

In DE-A-40 33 291, a process is described by means of which the aforementioned demands can be achieved in some respects. In this process, firstly preferably spherical shaped bodies are connected to one another to form a three-dimensional conglomerate of shaped bodies, thereafter a material different from the material of the shaped bodies is molded around the shaped bodies in order to form a three-dimensional framework, and subsequently the shaped bodies are removed so that only the three-dimensional framework is left. In subsequent process steps, the cavity system resulting from the removal of the shaped bodies can be again filled with a ceramic mass, for example, and subsequently the three-dimensional framework can be removed. Thus, by means of this process both a "positive" of the bone and the above described "negative" of the bone can be produced. The preparation of the conglomerate of shaped bodies (negative) serving as the starting material is, however, rather money- and time-consuming and not in any case reproducible.

DE-A-22 42 867 discloses a process for the preparation of implantable, porous, ceramic bone replacement, bone composite or prosthesis anchorage materials. In this process, firstly an "auxiliary framework" is prepared of spheres which approximately corresponds to the pores and pore connections of the finished material, and subsequently a castable ceramic mass is filled into the framework. After the ceramic mass has at least partially solidified, the auxiliary framework is decomposed and removed. The process for the preparation of the initial auxiliary framework made of spheres can be, however, at best standardized in a time- and money-consuming manner and is hardly reproducible.

SUMMARY OF THE INVENTION

Thus, an object of the invention consists in providing materials and processes for their preparation, by means of which it is possible to provide on the one hand a material with a three-dimensional framework of shell-like or trabecular structures as a positive, and on the other hand also its negative, i.e. a material consisting of shaped bodies connected to one another, as well as a combination of these two materials, wherein the porosity and the thickness of the supporting structures of the positive material as well as the configuration of the shaped bodies and their connections in the negative material can be exactly and reproducibly adjusted while taking into account the respectively required properties, such as dimensional stability and absorbability.

A further object of the invention consists in providing such materials and processes for their preparation which exhibit increased strength and/or permeability.

These objects are achieved by means of the present invention. The invention thus solves an old problem in material preparation, in particular in the preparation of materials for medicine. By means of the process according to the invention it is possible to simply and reproducibly prepare a porous material with a continuously porous framework having an adjustable porosity and an adjustable strength as well as material properties, such as solubility and absorbability, which are adapted to the respective requirements, wherein the pore system can optionally be filled with a different material.

As "positive", i.e. as material imitating the bone, the material according to the invention comprises a three-dimensional framework consisting of load-bearing shell-like structures which enclose cavities communicating with each other and adjustable in a predetermined manner. These cavities are adjustable in a predetermined manner in particular in that the space taken up by the cavities in the finished material is during the production process of the material firstly taken up by shaped bodies as space retainers, wherein the shaped bodies are appropriately selected and arranged in a mold depending on the demands on the pore system. The material according to the invention as "negative", which can be used, e.g., as an implant, comprises a three-dimensional composite of shaped bodies which are connected with one another via webs whose width and length are adjustable. The shape and structure of these "webs" will be explained hereinafter. The material as positive is producible in that the framework is formed around deformable shaped bodies which serve as space retainers for the cavities and form a "negative", and in that said shaped bodies are subsequently removed.

The finished material as negative can be produced by filling the framework, i.e. the positive material, and subsequently removing the framework.

Depending in the selected materials, it is also possible to form again a framework around said finished negative material, for instance by diffusing a castable material therein, and to remove the negative upon solidification of the castable material. The outer shape of the thus produced positive material corresponds to the framework of the aforementioned positive material but can be of a different material.

Hence, by combining different materials, both positive and negative materials can be prepared from a variety of absorbable and non-absorbable materials. The material according to the invention can be used, for instance, as an artificial bone, as an implant, as a filter and as a drug delivery system.

The use of the material according to the invention in the filter technology is therefore particularly advantageous since any desired porosity is adjustable and furthermore a macroscopically large-pore filter system can be combined with a microporous filter system if the basic material itself is porous. Moreover, the macroporosity and microporosity can be partially or completely filled with an actively absorbing material.

For specific purposes it may also be desirable to provide a material in which the positive and the negative of different materials are present together, for instance a material comprising a metal framework consisting of shell-like structures whose interconnecting pore system, i.e. the "negative" is filled with a ceramic mass, such as tricalcium phosphate or hydroxlapatite. When such a material is used, for instance as an implant, the bone firstly grows well onto the ceramics and a primary composite between bone and ceramics can be formed. The further ingrowth of the bone is also enhanced by the aforementioned effect of ceramics. In this connection, preferably absorbable ceramics is used, but the ceramics can also be non-absorbable. The material consisting of positive and negative can optionally also have a higher strength than the pure positive material.

As starting material for the process according to the invention, preferably deformable shaped bodies are used. For the shaped bodies, a material having a relatively low modulus of elasticity and being relatively easily deformable under pressure is preferred. The shaped bodies serving as space retainers for the cavity system of the finished porous material exhibit preferably the shape of spheres but can also be ellipsoids, granular elements or polygons or mixtures of such shaped bodies. The material for the shaped bodies is selected such that the shaped bodies can be easily removed later on in the further process, for instance chemically or physically.

The shaped bodies are firstly filled into a mold and optionally shaken and form a bulk. In this step, the shaped bodies are preferably not yet essentially deformed. It is not necessary either that the shaped bodies are chemically or physically connected with each other. It rather suffices that the shaped bodies are sufficiently pressed against each other during filling the form with a castable, extrudable or pourable material, which is, for instance, easily controllable by the appropriate adjustment of the injection pressure of the material or by generation of pressure in any other way. By the application of pressure, the shaped bodies are slightly pressed against each other and/or deformed. Depending on how much pressure is applied, the extent of the deformation of the shaped bodies and thus also the width or the cross-sectional area of their points of contact as well as their total configuration, which later in the finished porous material corresponds to the interconnecting pore system, can be easily and precisely adjusted and controlled. DE-A-40 33 291 also discloses the adjustability of the three-dimensional framework of trabecular structures; however, with the process according to the invention, the width or the cross-section of the webs by means of which the shaped bodies are connected with each other can be adjusted in the negative pattern much more precisely and reproducibly, since the contact pressure between the individual shaped bodies is not influenced by air and other undesired inclusions, as is the case when the individual shaped bodies are chemically or physically joined to form a conglomerate of shaped bodies. When in this connection the term "webs" is used, generally the connection between two adjacent shaped bodies contacting each other is meant. The more the shaped bodies are deformed and pressed against each other, the larger is the cross-section of the connection or "web" between the two shaped bodies under otherwise unchanged conditions. Thus, by means of the reproducible adjustability of the connections between the individual shaped bodies in the process according to the invention, the interconnecting porosity, i.e. the arrangement of the pores and their connection channels, can also be adjusted very precisely and reproducibly in the finished porous material, since the shaped bodies and their connecting webs serve as space retainers for the pores and their connections or penetration orifices. It is also ensured that the porosity in the finished material is interconnecting, i.e. that each of the individual pores are continuously in contact with each other. Some of the remarkable features of the process according to the invention are exactly the reproducibility and standardizability of the production with the result of an absolutely uniform structure exhibiting little variation, as well as the far simpler and cost-advantageous production of the material. It has become apparent that despite its better reproducibility and standardizability the material according to the invention can be produced in a fraction of the time necessary for the material according to DE-A-40 33 291.

The simple way in which the preparation of a material according to the invention can be performed is due to the use of easily removable deformable shaped bodies which do not have to be connected with each other but are only pressed against each other, for instance by the injection pressure of the injected material, wherein the width or the cross-section of the "web" between the shaped bodies in the conglomerate of shaped bodies can be reproducibly determined and adjusted, whereby a standardized interconnecting porosity can be produced in the finished porous material.

As material for the deformable shaped bodies, preferably an expandable synthetic material is used. A foamed material consisting of expandable polystyrene (EPS) is particularly preferred, but all other foamed or hollow-spherical shaped bodies consisting of synthetic material and exhibiting the appropriate deformability and easy solubility can also be used. The solubility of the shaped bodies can also be controlled by their porosity (microporosity).

The deformable shaped bodies have preferably a size between approximately 200 μm and several mm, for instance up to 5 mm, particularly preferred is a size between 200 μm and 3000 μm, between 500 μm and 3000 μm or between 1000 μm and 2000 μm. It is preferred to use a specific size fraction of shaped bodies, which is selected, for instance, by sieving or on account of their process of production, e.g. a size of approximately 1000 μm. By the selection of the size of the shaped bodies, the porosity of the finished porous material can be reproducibly, exactly and standardizably adjusted, also small pores of up to a pore size of far below 500 μm, for instance of down to 200 μm.

It is also possible to use a mixture of shaped bodies of various size and/or various morphology as starting material of the process according to the invention.

Other substances can optionally also be used as material for the shaped bodies, such as wax, gels, paraffins, collagens, chitin-like substances or mixtures of such substances, optionally binders having a gel-like character. The shaped bodies can also consist of a composite of finely-disperse material with an easily soluble hydrophilic or hydrophobic binder, wherein the binder can chemically be easily dissolved away.

Preferably, the individual shaped bodies themselves have a microporosity which is between 1 and 40%, preferably between 15 and 25%.

The material which is molded around the deformable shaped bodies should be castable, extrudable or pourable, in particular under pressure. When "castable" material is mentioned in the present description, this is intended to include any castable, extrudable or pourable material. A variety of materials can be used as castable material, depending on the purpose of use and depending on whether the castable material is only an intermediate step in the manufacturing process and is removed later on or whether the castable material forms part of the finished material, for instance the framework consisting of shell-like structures (positive) or the shaped bodies of the finished material (negative) which are interconnected via webs. As material for both the finished positive and the finished negative, for example ceramic materials or ceramic composite materials can be used, preferably such materials which exhibit a high density and can be subjected to sintering. For example, such ceramic materials can be used which are easily absorbed by the body after sintering. However, ceramic materials having a high density can also be used which are hardly or only very slowly absorbed after sintering. Preferred ceramic materials are hydroxylapatite, tricalcium phosphate and mixtures thereof. Hydroxylapatite and tricalcium phosphate as well as the mixtures thereof can preferably be mixed with binders, such as agarose, agar-agar, chitosan or gels, for instance in a ratio of 10:90 to 70:30, preferably approximately 50:50.

However, as castable material or as material for the shell-like framework (positive) or the shaped bodies (negative) connected via webs various other materials can also be used, for instance castable and extrudable plastics which can be both absorbable and non-absorbable, polylactates, polyglycolates, absorbable polyamine acids as well as mixtures thereof, collagens or similar materials or plastics on PMMA basis which are absorbable and/or dissolvable or non-absorbable and/or non-dissolvable in the body. Metals, metal alloys or metal composite materials are also preferred both as positive pattern comprising a trabecular metal framework and as negative pattern with a preferably spherical composite of shaped metal bodies comprising connection webs. In particular for the load transmission as replacement or partial replacement for bodies of vertebra for the fusion of bodies of vertebra, the material according to the invention consisting of shaped bodies, which are interconnected via webs and preferably consist of metal, has very favourable biomechanical properties, which are, for instance, more favourable than those in the open-pore or open-cell metal structure described in DE-C-31 06 917. When metal is used as material for the three-dimensional framework, the metal is preferably formed around shaped bodies of ceramics or gypsum. Silicone, caoutchouc derivatives or related polymers on rubber basis can also be used as material in particular for the three-dimensional framework of the porous material.

Basically, any materials whatsoever can be introduced into the negative or positive pattern, shell-like honeycomb constructions, for example, can be reproducibly and standardizably prepared, or polymorphous materials can be produced by mixing differently shaped deformable shaped bodies as starting material, for instance as implant material. Water-soluble shaped bodies, for instance, can be combined with meltable materials, or sinterable, castable material composites can be combined with water-soluble shaped bodies, or synthetic materials processable by injection moulding, ceramic materials or metals, metal alloys or metal composite materials can be combined such that the shaped bodies are in each case either physically or chemically or in any other way again removable and the three-dimensional shell framework is left as supporting framework. The supporting framework can subsequently be solidified, surface-treated or mechanically finished by physical or chemical methods. The mentioned metals, metal alloys or metal composite materials can be, for instance, castable or processable by centrifugal casting or vacuum investment casting. When, for instance, a ceramic negative pattern consisting of shaped bodies is combined with a metal casting in the form of a shell framework, this composite material can be very highly densified in the so-called HIP process and is mechanically very stable and capable of bearing considerable load. Even after the ceramics has been removed, the remaining trabecular structure or shell-like structure is very stable and capable of bearing extreme mechanical load, represents a very light bone implant through which bone can rapidly grow and which requires very little material. Upon solidification of the material surrounding them, the shaped bodies can be physically or chemically removed, for instance in a water bath, a washing machine or by solvents, wherein in the case of the use of foamed polystyrene or a similar foamed synthetic material, acetone is particularly appropriate as solvent.

For those materials which are removed in the course of the manufacturing process and are not part of the finished material, other substances can also be taken into account, for example gypsum, which can be particularly easily and rapidly processed and is furthermore cheap.

The castable material is particularly well distributed in the bulk of shaped bodies during the filling step, when the shaped bodies are hydrophobic and the castable material is hydrophilic.

The total porosity of the finished porous material is preferably between 50 and 90%, more preferably between 65 and 85%. The material for both the finished shell framework (positive) and the shaped bodies of the negative material, can have a microporosity, for instance between 1 and 40%, more preferably between 15 and 25%.

For specific purposes of use, it can be advantageous to render the passage orifices between the individual pores of the interconnecting pore system of the porous material variable or to enlarge them. This is in particular advantageous when bone cement is sucked into the material or sucked through it or if a faster bone ingrowth is to be attained, wherein optionally a lower resistance to pressure of the material can be accepted. In order to enlarge the cross-section of the connections or penetration orifices between the individual pores, the material with the interconnecting pore system is subsequently chemically treated. A particularly advantageous chemical treatment is the influence of an acid or lye flowing through the pore system. By means of this chemical treatment first of all the thin lamellae of the framework at the point of contact between two pores are attacked and dissolved and thus the cross-section of the pores is enlarged. By the selection of the used chemical agent, the adjustment of its dilution and in particular by varying the duration of the influence of the chemical treatment on the composite material, the original pore connections can be enlarged in a controlled and defined manner and adapted to the requirements. Advantageously, it is proceeded such that a diluted acid flows through the material for a short time so that only the pore connections are enlarged but the structure of the framework as such is not essentially affected or modified. When according to the invention the framework comprising an interconnecting pore system serves as starting or intermediate material for a material consisting of interconnected shaped bodies ("negative"), an enlargement of the cross-section of the connections or "webs" between the individual shaped bodies is effected by an enlargement of the penetration orifices between the pores of the interconnecting pore system of the framework, after a castable, extrudable or pourable material is filled into the pore system for forming the shaped bodies. Thus, the strength of the finished negative material consisting of shaped bodies connected with each other via webs is achieved.

If a particularly high mechanical stability of the "positive" or "negative" material according to the invention is aimed at, massive portions can advantageously be provided in the interior of the material. Apart therefrom, the interconnecting pore system of the framework in the positive material and the configuration of connected shaped bodies in the negative material can be maintained. Preferably, the massive portions in the interior of the material are designed as massive struts, such as reinforcing struts or trajectories. The massive portions are preferably approximately cylindrical and their cross-section has a diameter of preferably approximately 0.5 to 3 mm. The axis of the cylinder preferably extends in the same direction as the expected main load of the material. The massive portions preferably extend longitudinally through the entire material, but can also extend only through part of the material. There can be one or more of such reinforcing struts, for instance 2 to 6, preferably 3 or 4 struts. The massive struts cause in particular an increase of the pressure stability of the material while maintaining the high porosity and bone ingrowing capability of the positive material.

For preparing the material reinforced with the massive portions, both deformable shaped bodies and shaped bodies made of a non-deformable or little deformable material, such as sugar, can be used as starting material. Preferably, in this method, too, deformable shaped bodies are used. In order to prepare the massive portions in the "positive" material, cannulas, such as filling cannulas, are introduced into the mould during the first filling of the mould with the shaped bodies, and the shaped bodies are arranged around these cannulas. Subsequently, the mold is filled with the castable material via the cannulas and/or, as usual, from outside. During the filing, the cannulas are successively removed from the mold and in the material massive portions are formed at those parts of the mould which were before occupied by the cannulas in addition to the framework exhibiting an interconnecting pore system. The removal of the cannulas and the filing with castable material are coordinated over time. The framework of shell-like structures and the massive portions are formed in one casting step so that the entire material is made of a homogeneous material.

When producing the "negative" material with massive portions, space retainers are introduced into the mould together with the shaped bodies, for example in the form of small pipes. These small pipes can either be hollow or massive but have in any case the same outer shape and design as the massive portions to be formed later on in the material. During the subsequent filling of the mould with the castable material, the small pipes are enclosed. Subsequently, these small pipes, which serve as space retainers, are removed, for example by extracting them from the mold or by removing them chemically or physically. The extracted space retainers leave behind cavities within the framework formed. During the subsequent filling of the framework with the castable material forming the shaped bodies, these cavities are filled to form massive portions. Thus, also in this method, the massive portions and the surrounding material made of interconnected shaped bodies are formed in one casting step so that the entire material is homogeneous. However, it is also possible both in positive and the negative material to form the massive portions of different material, e.g., if this is preferred for reasons of strength. For example, fibers, e.g., of ceramics, coal, glass or metal, can be introduced into the massive portions for reinforcement. The material matrix of the massive portions can be of the same material as the surrounding framework and/or the shaped bodies or of a material differing therefrom. In order to form the massive portions of a material differing from that of the surrounding framework or the shaped bodies, the massive portions are produced in a separate method step. The place retainers are for example at first left in the mold until the material is cast, and only then is another material filled in. Massive portions in the form of metal struts are for example particularly preferred which portions are embedded in a negative material of shaped ceramic bodies in order to increase the bending strength. During the final sintering step the ceramic material shrinks on the metal such that ceramics and metal are permanently joined together.

The outer shape of the material according to the invention is optional and is in particular determined by the design of the casting mold used in the method according to the invention. By varying the initial filling volume of the casting mold with the shaped bodies and the number and direction of the injection channels of the castable material, massive portions can purposefully be formed at one or more of the outer surfaces of the material, for example in the form of a thin massive lid. What is called a tricortical cuboid is particularly preferred, i.e. a cuboid made of a porous material in which a massive, thin outer layer is formed at two opposite surfaces of the cuboid and at the surface connecting these surfaces. This massive layer can for example have a thickness of 0.5 to 3 mm, preferably at least 1 mm. Such tricortical cuboids are of particular advantage when using them as bone replacement materials or artificial bones, such as pelvic bone replacement materials.

Preferably, the finished material comprises at least one active ingredient, in particular if the material is used in medical engineering, e.g. for the production of implants and bone replacement materials, as a filter system or an active-ingredient carrier in the form of what is called a "drug delivery system". The finished material comprises preferably 0.01 to 10% of the active ingredient, which is preferably protractedly releasable from the material. For example, the structure of the positive and/or the composite of spheres of the negative, which is connected via webs, can be coated in layers with one or more layers of one or more active ingredients. The macro- or microporosity of the active ingredient can also be reproducibly filled with a mixture of a binder and an active ingredient, the active ingredient being preferably protractedly releasable in the body over a defined period of time.

The added active ingredients can purposefully induce the vessel or bone ingrowth, purposeful treat a local tumor or purposefully contribute to the treatment of an infection. The concentrations obtainable with the present invention by far exceed those of an active ingredient, such as an antibiotic, which could be achieved with a systematic treatment. By a suitable combination with binders or by changes in the porosity, the delayed release of the active ingredient can be adjusted.

As active ingredients, gentamycin, glindamycin, a gyrase inhibitor or another antiobiotic or a combination of two or more different antibiotics can be used. A growth-stimulating active ingredient can also be used as active ingredient, such as an active ingredient of the type of a "bone morphogenetic protein", a growth factor or another chemotactically or hormonally active factor which causes the sprouting or vessels or the differentiation of bone-forming cells and moreover prevents bone destruction. Furthermore, a cytostatic, a combination of several cytostatics or a combination of cytostatics with other active ingredients, such as antibiotics or hormones, can be used.

The macropore system of the porous material can also be filled with activated charcoal or another highly porous adsorbant.

Moreover, a filler, preferably in the form of filler particles can be added to the material according to the invention. As filler particles, 1 to 95%, preferably 1 to 80% of tricalcium phosphate or hydroxylapatite or a mixture thereof or another calcium-phosphate composite or calcium composite can be used. The particle size is preferably 20 to 300 µm and more preferably 50 to 250 µm and the pore volume of the porous filler particles is preferably 0.1 to 0.8 ml/g. The addition of filler particles is particularly preferably when using extrudable plastics materials. If the material according to the invention is made of plastics or metals, a coating with tricalcium phosphate and/or hydroxylapatite is desirable. This is of particular advantage if it is desired that the bone grows through the material. Under load, the bone converts the deformation energy at the interface of smooth implants into a relative motion, which leads to a bone absorption, whereas no such relative motion occurs in the case of rough surfaces, such as surfaces which are coated in such a way.

Activated charcoal or another higher gas- and/or fluid-absorbing material can also be used, preferably in a concentration between 1 and 80% or 5 to 80%.

The following methods are particularly preferred according to the present invention:

A process for the preparation of a material having a three-dimensional shell-like framework, comprising the following method steps: pressing preferably spherical deformable shaped bodies together to form a three-dimensional packing of shaped bodies; forming a material which differs from the material of the shaped bodies around the shaped bodies while deforming the shaped bodies for forming a three-dimensional shell-like framework and removing the shaped bodies so that merely the three-dimensional shell-like framework remains and forms the material.

A process for the preparation of a material with shaped bodies connected via webs, comprising the following method steps: formation of a three-dimensional packing of shaped bodies by pressing deformable shaped bodies together; forming a three-dimensional framework made of a wax or a readily meltable polymer around the shaped bodies; curing the framework made of a wax or a readily meltable polymer; chemical removal of the shaped bodies; filling the continuous cavity system formed by the removal of the shaped bodies with a ceramic mass; and removing the framework made of wax or the readily meltable polymer by applying heat. In this method, ceramic spheres are preferably formed in the cavities. The ceramic spheres can be converted into β and α Whitlockit tricalcium-phosphate composites by the application of heat or can be joined by sintering to form solid bodies of spherical conglomerates, e.g. of hydroxylapatite.

A process for the preparation of a metal material of a shell-like framework, comprising the following steps: production of a bulk material of deformable plastics spheres, e.g., of polystyrene; pressing the spheres together and filling the mould with wax; removing the plastics spheres with a solvent, such as acetone; drying the wax framework; filling a ceramic mass, such as a gel-like mixture of tricalcium phosphate and a binder, into the wax framework; removing the wax in an oil bath and solidifying the ceramic mass; subsequently sintering the ceramic mass in a furnace at a heating rate of approximately 1° C./min up to a temperature of approximately 1300° C. for about 24 hours; placing the formed ceramic body into a box-type furnace and filling it by centrifugal casting with a CoCrMo alloy; sandblasting the ceramic-metal composite and removing the ceramic material with an acid, such as hydrochloric acid.

A process for the preparation of a metal material consisting of shaped bodies connected with each other by means of webs, comprising the following method steps: production of a bulk material of deformable plastics spheres, such as foamed polystyrene spheres; compression of the spheres; filling the volume around the spheres with a ceramic mass, removing the spheres with a solvent, such as acetone; drying, preferably in an ascending acetone series; sintering the formed ceramic shell-like framework in a furnace at a heating rate of 1° C./min up to a temperature of 1300° C. for about 24 hours; placing the ceramic framework into a box-type furnace and filling the macropore volume with a metal alloy, preferably CoCrMo, by centrifugal casting or vacuum investment casting; removing the ceramics in an acid bath, such as hydrochloric acid.

DESCRIPTION OF THE PREFERRED EMBODIMENTS

A particularly preferred starting material for the deformable shaped bodies is Styropor, such as Styropor® F414, i.e., a foamed material of expandable polystyrene (EPS), which has been foamed with pentane as expanding agent. Preferred weights per unit of volume are between 17 g/l and 70 g/l, preferably approximately 20 g/l to 35 g/l. The grain sizes of the foamed material range between 200 $\mu$m and 3000 $\mu$m.

In order to obtain a dimension figure for a suitable deformability of the deformable shaped body, experiments were made for determining an E-modulus-like parameter for several shaped bodies. For this purpose, the respective shaped bodies were poured into a cylindrical vessel up to an initial height of 84.3 mm. Subsequently, a force F is applied to the bulk material via a die, and the compression, i.e. the change in the initial height, is registered as a function of the applied force. An E-modulus-like quantity is then determined via the formula $$E = \frac{F \times l}{A \times \Delta l},$$

in which

E=E-modulus-like quantity

F=force in N

A=surface of the cylinder in mm$^2$ l=initial height (84.3 mm)

$\Delta l$=change in the initial height in mm.

The experiments results for several foamed polystyrene types, which differ, e.g., in their weight per unit of volume, the kind of foaming and their particle size, in values for E of about 0.5 to approximately 1.2 N/mm$^2$. Such an elasticity is particularly preferred. The elasticity can, however, be also higher or lower by approximately the factor 10. In contrast, the value E of, e.g., various sugar types is approximately 20 to 180 N/mm$^2$, the sugar bodies being however partly crushed due to the application of force.

As castable material, a mixture of hydroxylapatite powder and an agar solution in a ratio of 10 g powder/7 ml to 25 ml agar solution, preferably 10 g powder/20 ml agar solution, is preferably used. The agar solution preferably consists of a mixture of bi-distilled water with agar-agar in a ratio of 20 ml to 50 ml/1 g, preferably in a ratio of 40 ml/1 g.

Figure 1:
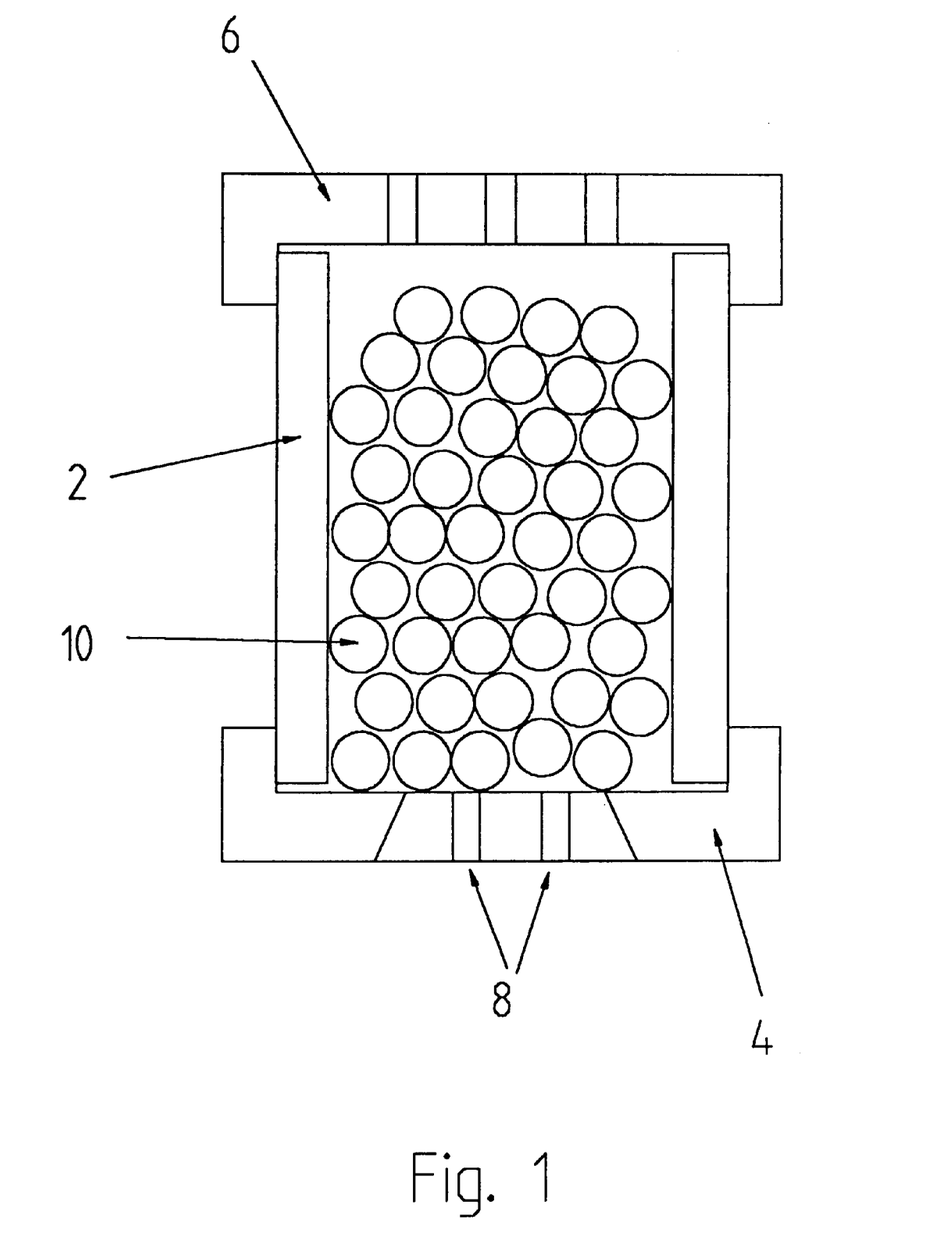
FIGS. 1 to 3 show the filling of deformable shaped bodies into a mold and the filling of the mold with a castable material.
Figure 2:
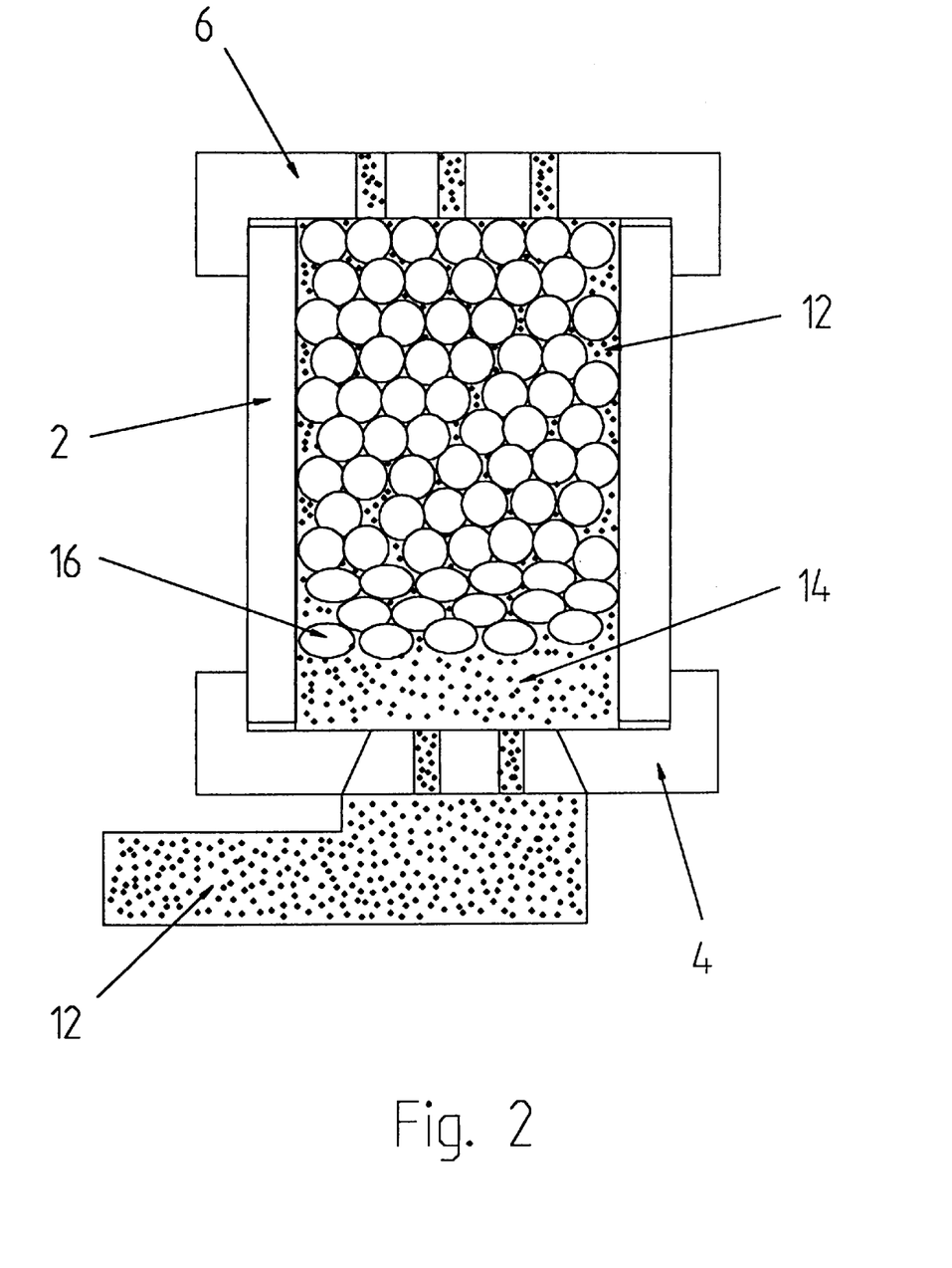

FIG. 1 schematically shows a mold 2 with a bottom 4 and a lid 6 as well as filling channels 8. Foamed shaped polystyrene bodies 10 having a spherical shape are filled into the mold 2. When filling the shaped bodies into the mold 2, the latter is only filled to such an extent that the shaped bodies are not subjected to pressure and are not deformed. Subsequently, the mold 2 is filled from the bottom with a ceramic mass 12 as castable material having the aforementioned composition, as shown in FIG. 2. On account of the viscosity of the ceramic mass, the shaped EPS bodies are subjected first to pressure acting in the axial direction to the top such that the shaped bodies are pressed against each other. The result of the reduction in volume thus created is that at the bottom 4 of the mold 2 a polystyrene-free zone 14 is formed which is only filled with ceramic mass and later on forms a dense and massive lid of the finished porous material. Depending on the initial filling volume of the mold 2 and the viscosity of the ceramic mass, the height of the zone 14 and thus the thickness of the lid of the finished material can be varied. The initial filling volume can, however, also be selected such that the entire material formed is porous and no massive lid is formed.

Figure 3:
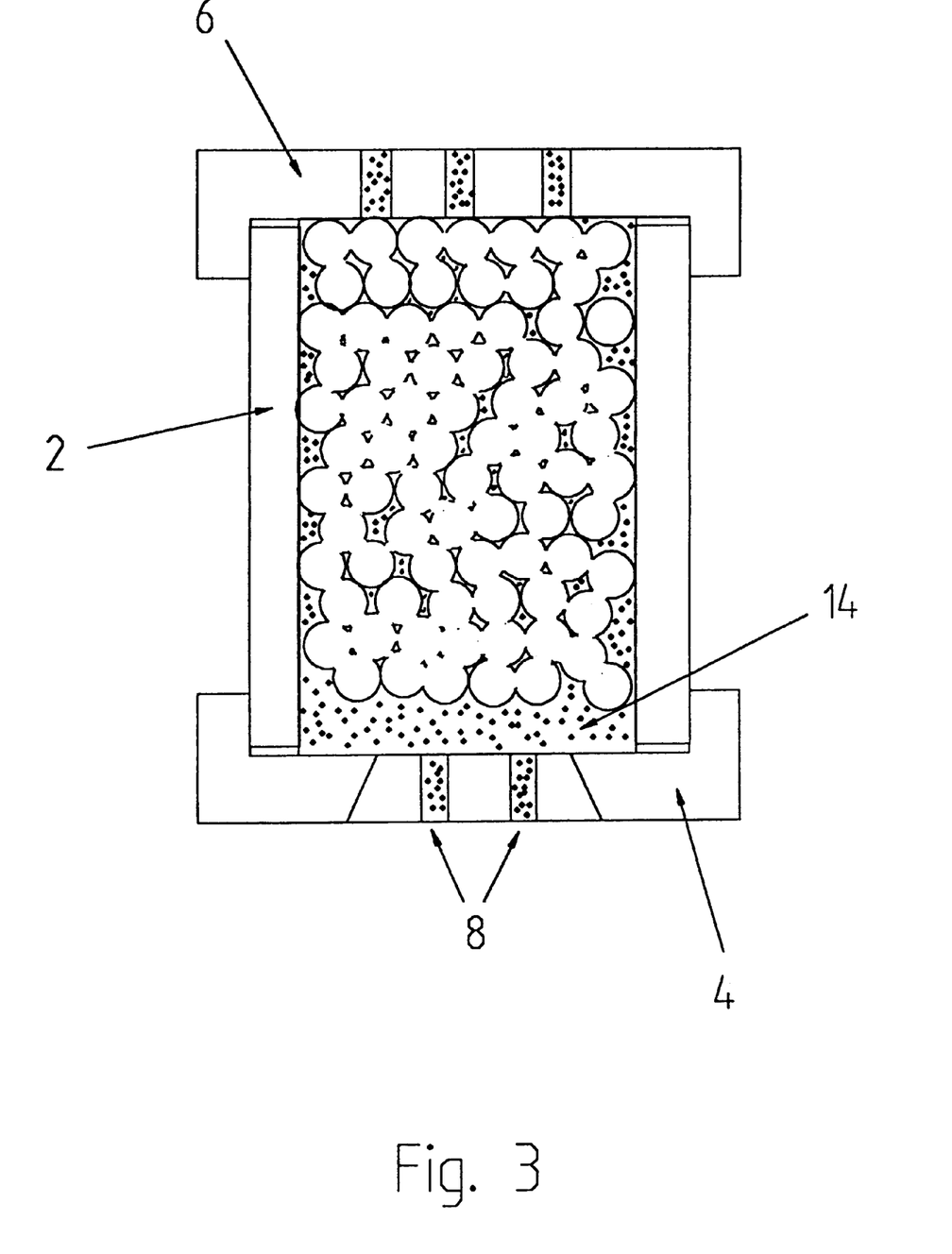

On account of the unidirectional pressure occurring when the ceramic mass is filled in, the deformable EPS spheres 10 are probably first deformed to oval bodies, as shown, e.g., in FIG. 2 by means of the body 16. After completion of the filling step, however, a pressure which has a uniform value in all directions, i.e. an isostatic pressure is formed within the mould. In combination with the elasticity of the shaped EPS bodies and the still soft ceramic mass, this pressure leads to a relaxation of the deformed EPS bodies into their spherical shape. The situation upon completion of the filling step is shown in FIG. 3. After the solidification of the ceramic mass, an isotropic distribution of the shaped EPS bodies is observable. Upon removal of the shaped EPS bodies, for example by means of acetone, the remaining ceramic material has a completely homogeneous structure and exhibits interconnecting spherical pores. The shapes of the pore system and its connection channels correspond to the shapes of the shaped-body composite and its connection channels. The orifices between the pores can subsequently be widened by means of a chemical treatment, for example with an acid or a lye.

Figure 4:
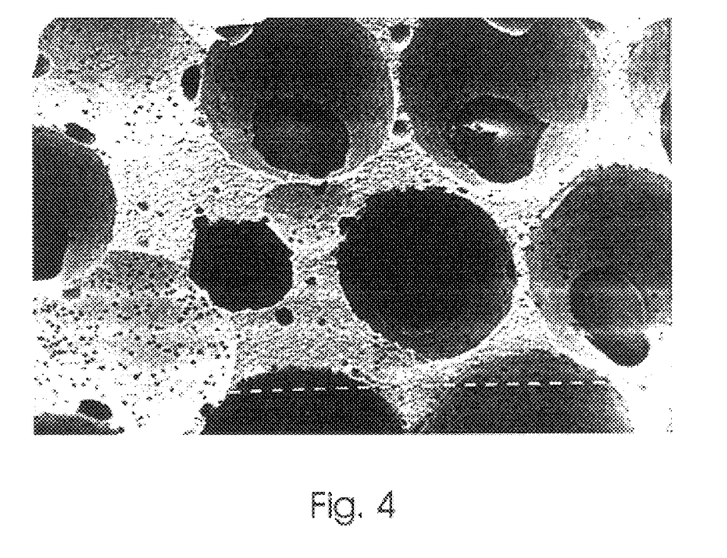
FIGS. 4 and 5 show electron-microscopical pictures of the material according to the invention.

FIG. 4 shows an electron-microscopical picture of a material according to the invention with a three-dimensional framework, the shell shape of the framework being clearly perceivable. A line in FIG. 4 corresponds to 100 $\mu$m.

Figure 5:
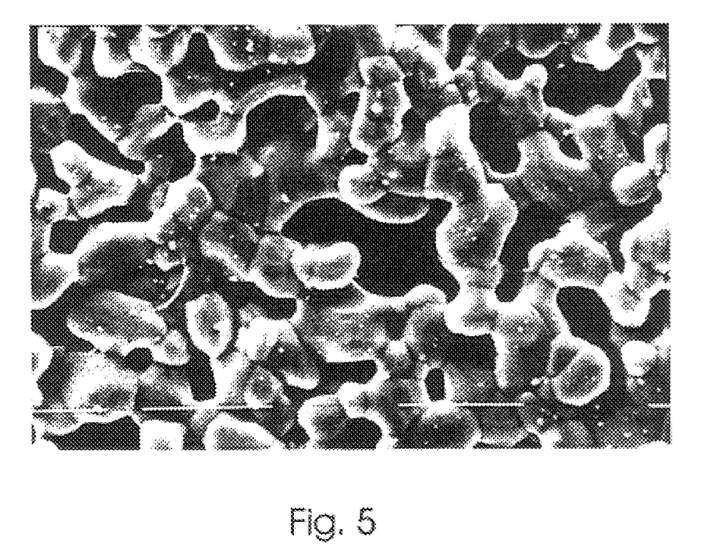

FIG. 5 shows a further enlarged view of the surface structure. In FIG. 5 a line corresponds to 10 $\mu$m.

Figure 6:
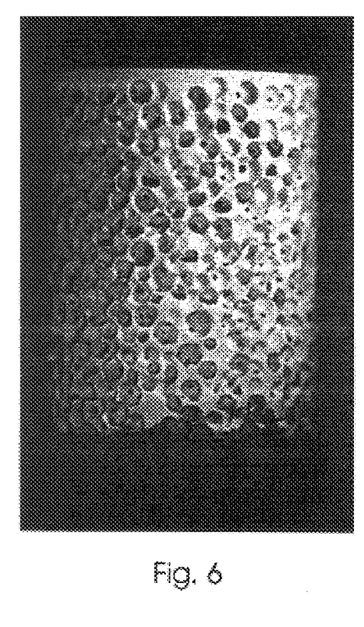
FIGS. 6 to 9 show side and top views of the material according to the invention.

FIG. 6 shows a 5 to 6-fold enlargement of a side view of a cylinder of relatively macroporous positive material with a shell-like framework and an interconnecting isotropic pore system.

Figure 7:
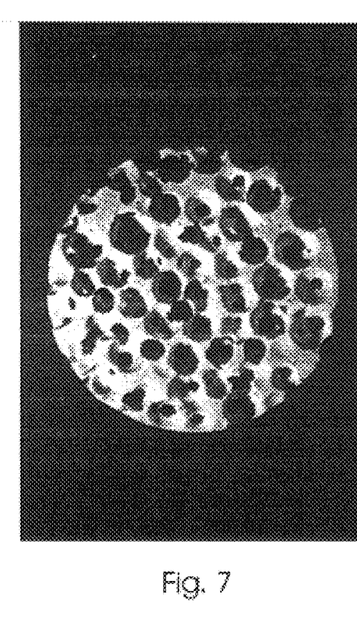

FIG. 7 shows a top view of such a cylinder. In FIGS. 6 and 7, the homogeneous isotropic distribution of the interconnecting pore system as well as the trabecular or shell-like framework, which is adapted to the bone structure, are clearly evident.

Figure 8:
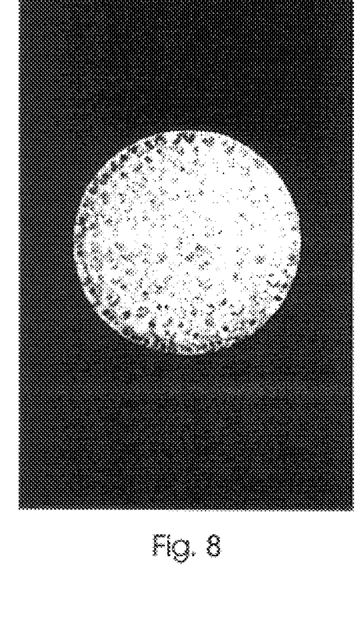

FIG. 8 shows a top view of a cylinder of a relatively microporous "positive" material. The shell-like framework and the interconnecting isotropic pore system thereinbetween is also clearly perceivable in this figure.

Figure 9:
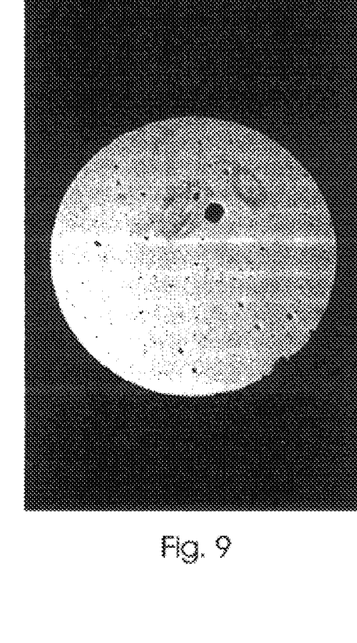

FIG. 9 shows a top view of a dense and massive lid of a "positive" material according to the invention. As explained above in connection with FIG. 2, such a dense and massive lid (cover) can be achieved in that when filling the mold with the castable material, an end portion of the mould is completely filled with the castable material and the deformable shaped bodies, which serve as space retainers for the pore system, are completely displaced from this end portion. A material according to the invention having such a lid is, e.g. particularly advantageous for use as a plug in the medullary canal. Of course, it is also possible by means of suitable measures during the production to provide both end portions or different portions of the material volume, for example along the generated surface in the case of a material with cylindrical shape, with such a cover to the effect that the material is in this portion not porous but dense and massive.

Figure 10:
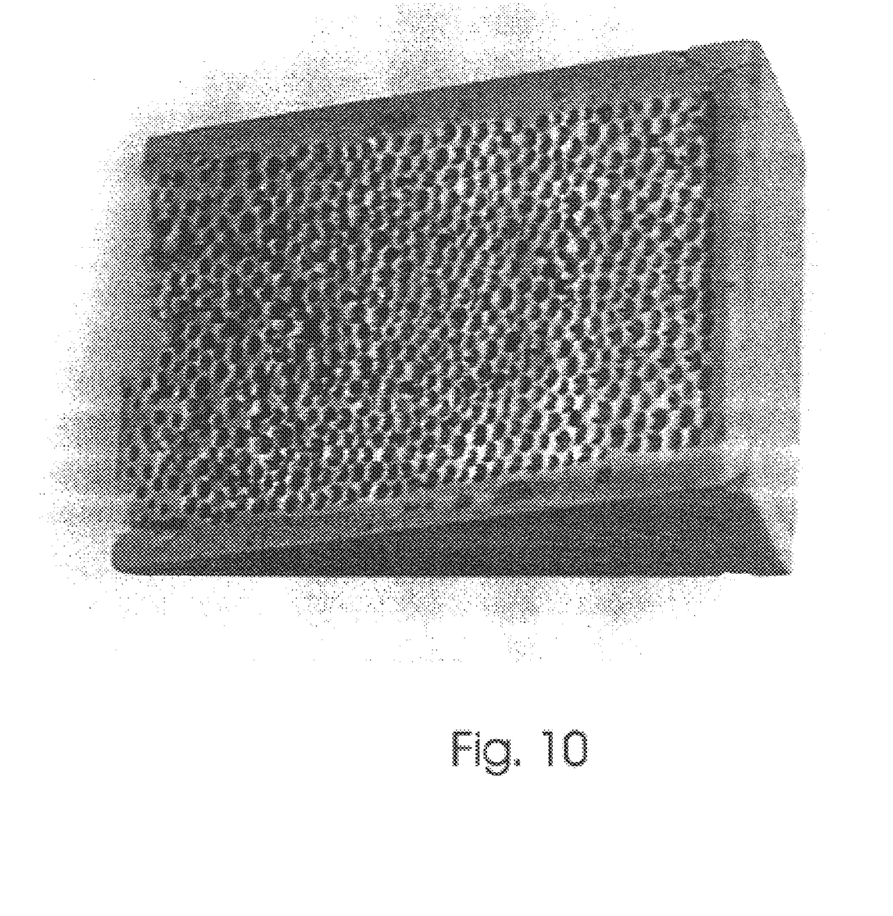
FIG. 10 shows a view of the material according to the invention in the form of a tricortical cuboid.

FIG. 10 shows an approximately 2- to 3-fold enlargement of a tricortical cuboid with a porous "spongy" inside, two opposing surfaces and an outer surface of the cuboid connecting the latter being provided with a thin massive layer. Such tricortical cuboids have an excellent resistance to pressure. The pressure resistance of tricortical cuboids having a base of 15×15 mm and a height of 7 mm was measured. The experiments were carried out on a universal testing machine Instron 1000 at a speed of load application of 5 mm/min in each case. A such dimensioned, completely porous ceramic cuboid according to the invention has a pressure resistance of about 2 to 4 MPa. A tricortical cuboid which has three massive outer surfaces and was moreover treated for 20 seconds with 25% HCl in order to enlarge the pores has a pressure resistance of 12.2 MPa. A further tricortical cuboid with a partly massive inner structure, i.e. with massive reinforcing struts, and exhibiting the same dimensions has a pressure resistance of 26.2 MPa.

Figure 11:
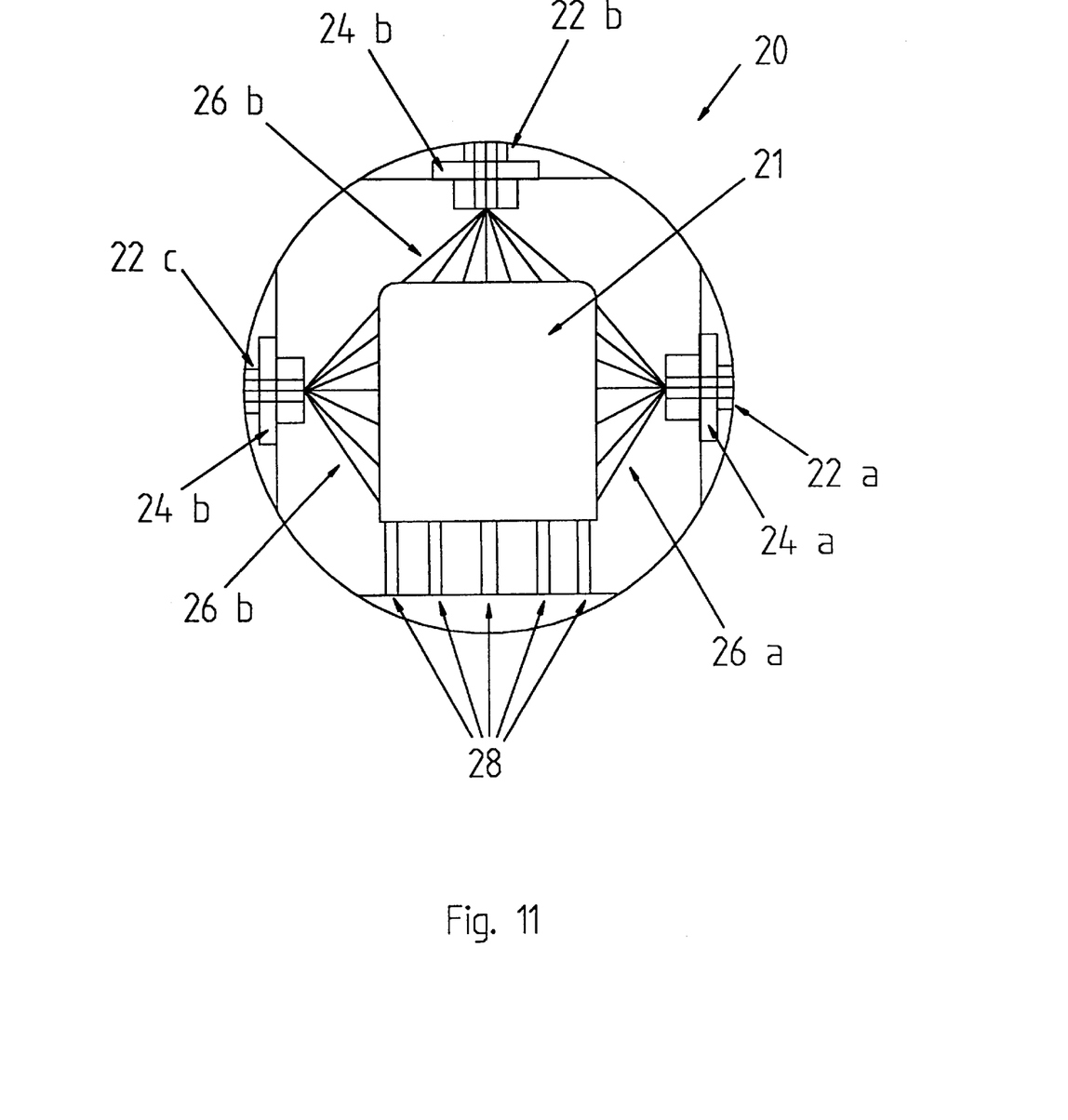
FIG. 11 shows a schematic view of a mold for producing a tricortical cuboid.

FIG. 11 schematically shows an injection mold 20 with an inner part 21 for producing a tricortical cuboid. The injection is carried out simultaneously at three sides via injection channels 22*a, b, c* and distribution connections 24*a, b, c.* Reference signs 26*a, b, c* indicate that each injection is distributed in a fan-like manner to the three impact surfaces where the massive outer surfaces of the tricortical cuboid are formed. Ventilation bores 28 are provided at the "free" side face.

EXAMPLE 1

Production of a material (negative) consisting of ceramics for use as a hollow bone-replacement material implant having a reproducible macro- and microporosity Spheres consisting of foamed polystyrene (EPS), such as Styropor® F 414, having a size of approximately 1000 $\mu$m after screening are poured into a cylindrical mould. Wax heated to 75° C. is diecast into the mould via a top gate. After curing the wax, the polystyrene is removed by means of acetone, subsequently, the wax framework is air-dried and then completely filled with a ceramic mass. The ceramic mass consists e.g. of 5 g of tricalcium phosphate or hydroxylapatite or a mixture thereof and 7 ml of a solution which can be made up of 2 g agar-agar and 80 ml water. The wax is subsequently removed from the wax/ceramic molded blank in an oil bath at temperatures of 100° C., and the remaining ceramic mass is solidified for 6 to 7 hours. The basic body thus obtained is sintered in a pottery kiln at a heating rate of 1° C./min up to 1300° C. for about 24 hours and subsequently stepwise cooled for further 24 hours. The ceramic implant thus formed and consisting of tricalcium phosphate, hydroxylapatite or a mixture thereof is what is called a "negative implant" and forms a three-dimensional composite of spheres interconnected via wide webs. Such an implant can in particular be advantageously used for high load transmissions and has pressure resistance of up to 10 MPa, which is extremely high for porous ceramic materials.

EXAMPLE 2

Production of a porous material (positive) made of ceramics for use as a bone replacement material having a continuously interconnecting pore system and a trabecular structure Spheres made of foamed polystyrene (EPS), such as Styropor® F 414, having a diameter of about 1000 $\mu$m are poured into a cylindrical vessel and shaken. By means of a top gate, a ceramic mass, which can have the composition according to Example 1, is diecast into the mould and subsequently evacuated. The mold ceramics-polystyrene blank is subsequently cured for half an hour in a refrigerator and then taken out of the refrigerator, and the polystyrene spheres are removed in an acetone bath. After air-drying over acetone, the green compact is sintered for about 24 hours at a heating rate of 1° C./min. in a pottery kiln up to a temperature of 1300° C. Subsequently, it is cooled stepwise for further 24 hours. Then, the ceramics implant which comprises continuously uniform interconnecting pores and has a trabecular or shell-like framework is finished.

EXAMPLE 3

Production of a porous material (positive) made of metal for use as a metal implant structured like the spongy substance Spheres of foamed polystyrene (EPS), such as Styropor® F 414 are poured into a vessel and shaken. The volume inbetween the spheres is filled with wax. The wax is diecast into the vessel by means of a top gate at a temperature of 75° C. Subsequently, the wax framework is cured, the polystyrene is removed in a acetone bath and subsequently the remaining wax framework is dried. Then, a ceramic mass is cast into the wax framework (positive), such as tricalcium phosphate, a mixture of tricalcium phosphate and hydroxylapatite or a mixture of pure hydroxylapatite and a gel-like substance as a binder; the ceramic mass can for example have the composition according to Example 1. Subsequently, the wax is removed in an oil bath at 100° C. and the remaining ceramic mass (negative) is solidified for 6 to 7 hours. The green compact thus produced is sintered in a pottery kiln for about 24 hours at a heating rate of 1° C./min and at a temperature of up to 1300° C. and then carefully cooled for further 24 hours. The ceramic body thus formed and made of spheres with connection webs having a defined cross-section is placed in a mold into a box-type furnace and filled with a CoCrMo alloy in a centrifugal- or vacuum investment-casting method at 1000° C. After removal, the formed ceramics-metal composite is sandblast, and subsequently the ceramics is removed in a hydrochloric acid bath. The implant shows a trabecular or shell-like framework with a standardized and reproducible interconnecting pore system formed thereinbetween which system has approximately spherical pores.

EXAMPLE 4

Production of a material (negative) made of metal for use as a vertebral replacement material Spheres of foamed polystyrene (EPS), such as Styropor® F 414, having a diameter of about 1000 $\mu$m are poured into a cylindrical vessel and shaken. By means of a top gate, a ceramic mass is diecast into the free volume between the spheres. Subsequently, the mold blank is hardened in a refrigerator for 30 minutes, the polystyrene spheres are subsequently removed in an acetone bath and the molded blank is dried over acetone. Subsequently, the remaining ceramic body (positive) is sintered in a pottery kiln at a heating rate of 1° C./min for about 24 hours at a temperature of up to 1300° C. Then the kiln is cooled for further 24 hours, and the ceramic positive is removed and subsequently filled with a CoCrMo alloy in a box-type furnace at 1000° C. in a centrifugal casting process. After its removal, the ceramic-metal composite thus formed is sandblast and then the ceramics is removed in an acid bath. The obtained metal framework (negative) forms a composite of spheres which are interconnected via defined wide webs and forms a continuously three-dimensional framework of spheres. This structure can be considered particularly advantageous for the load transmission and the ingrowth of bone trabecula in their physiological morphology. Such an implant is moreover highly stable and can directly be used as a vertebral replacement material.

In the aforementioned examples, gypsum can, e.g., also be used instead of the aforementioned ceramic mass, if the mass is removed later on and does not constitute part of the finished material, such as in examples 3 and 4. The use of gypsum is particularly inexpensive and unproblematic since gypsum cures quickly and can simply be processed. Gypsum is usually stable at temperatures of up to about 1050° C. and can therefore be used in combination with metals or metal alloys whose melting temperature is maximally 1050° C.

EXAMPLE 5

Implant reinforced by struts and trajectories

For vertebral replacement materials or for blocking two bodies of vertebra after a vertebral-disk excision, bone cubes or cuboids, which have to take up very high forces of pressure, are used. In the case of such surgical interventions, there are different types of remainders of bodies of vertebra. If there are still cortical elements, an implant is preferred which can be ingrown starting from its periphery from all sides. In such a case, a bone-replacement material implant without cortical proportions has to be used. In order to impart the necessary pressure resistance to the implant such that it withstands the aforementioned high stresses, the implant is reinforced in the axial direction with massive struts according to the invention.

What is claimed is:

1. A material comprising a shell-like framework and an interconnecting pore system formed between portions of the framework, the composite material produced by a process comprising the following process steps:

(a) filling deformable shaped bodies of predetermined shape into a mold for forming a bulk of the deformable shaped bodies with the bodies in contact with other bodies;

(b) filling the mold with castable, extrudable or pourable base material and solidifying the base material, the filling step causing the bodies to be pressed against one another and deformed in shape by pressure occurring during filling the base material into the mold wherein the base material fills the space between the deformable shaped bodies, and (c) removing the deformed bodies from the solidified base material, wherein the solidified base material forms the framework of shell-like structures with an interconnecting pore system determined by the shape of the deformable bodies.

2. The material according to claim 1, which has the shape of a tricortical cuboid.

3. The material according to claim 1, wherein the deformable shaped bodies are made of an expandable synthetic material.

4. The material according to claim 1, wherein the deformable shaped bodies are made of polystyrene.

5. The material of claim 1, wherein the deformable shaped bodies are spherical, elliptical, granular or polygonal or their non deformed condition.

* * * * *